United States Patent [19]

McCluer et al.

[11] Patent Number: 4,895,838

[45] Date of Patent: Jan. 23, 1990

[54] METHOD FOR PROVOKING ANGIOGENESIS BY ADMINISTRATION OF ANGIOGENICALLY ACTIVE OLIGOSACCHARIDES

[75] Inventors: Robert McCluer, Acton; Nicholas Catsimpoolas, Newton Center; Michael Klibaner, Brookline; Ann Griffith, Newton Center, all of Mass.; Robert Sinn, New York, N.Y.

[73] Assignees: Trustees of Boston University, Boston, Mass.; Angio-Medical Corporation, N.Y.

[21] Appl. No.: 165,809

[22] Filed: Mar. 9, 1988

[51] Int. Cl.⁴ .................... A01N 43/04; C07K 13/00; C07K 3/06; A61K 31/715
[52] U.S. Cl. ........................ 514/54; 514/53; 514/56; 514/61; 530/363

[58] Field of Search ............... 514/54, 53, 56, 61; 530/363

[56] References Cited

U.S. PATENT DOCUMENTS

| | | | |
|---|---|---|---|
| 4,057,685 | 11/1977 | McIntire | 530/363 |
| 4,401,662 | 8/1983 | Lormeau et al. | 514/54 |
| 4,496,550 | 1/1985 | Lindahl et al. | 514/54 |
| 4,710,490 | 12/1987 | Catsimpoolas et al. | 514/25 |

Primary Examiner—Ronald W. Griffin
Assistant Examiner—Everett White
Attorney, Agent, or Firm—Felfe & Lynch

[57] ABSTRACT

A method for causing or increasing angiogenesis is described. The method involves administering to a subject, such as a human being in need of angiogenesis an angiogenically effective amount of an angiogenically effective, pharmaceutically acceptable oligosaccharide or mixture of oligosaccharides.

22 Claims, No Drawings

METHOD FOR PROVOKING ANGIOGENESIS BY ADMINISTRATION OF ANGIOGENICALLY ACTIVE OLIGOSACCHARIDES

FIELD OF THE INVENTION

This invention relates to a method for causing or increasing angiogenesis in a subject in need of angiogenesis or increased angiogenesis via administration of an angiogenically effective amount of a pharmaceutically acceptable oligosaccharide with angiogenic activity.

BACKGROUND AND PRIOR ART

Interest in angiogenesis is evidenced by the vast amount of literature available on the subject, some of which is over one hundred years old. See, e.g., Virchau, R., *Die Krankhaftern Geshwulste,* Hirshwald, Berlin (1863); Thierisch, C., *Die Hautmit Altas,* Leipzig (1865). "Angiogenesis" is defined as the process by which new blood vessels are formed, with accompanying increased blood circulation. Much of the research in this field over the past ten years has concentrated on identifying and purifying naturally occurring substances which cause angiogenesis Examples of the literature in this area include Weiss, et al., Br. J. Cancer 40: 493–96 (1979); Fencelau, et al., J. Biol. Chem. 256: 9605–9611 (1981); McAslan, et al., Exp. Cell Res. 119: 181–190 (1979), which show that angiogenic factors are present in tissues of pathological origin, such as tumor cells. Kumar, et al., Lancet 2: 364–367 (1983); and Brown, et al., Lancet 1: 682–685 (1980), show an angiogenesis factor in synovial fluid of arthritis patients, while Hill, et al., Experentia 39: 583–585 (1983) show one in vitreum, of arthritic patients. Banda, et al., Proc. Natl. Acad. Sci. 79: 7773–7777 (1982), teach one in wound fluid. Additional teachings in this field include those of D'Amore, et al., Proc. Natl. Acad. Sci. 78: 3068–3072 (1981); Kissun, et al., Br. J. Ophthalmol. 66: 165–159 (1982); DeCarvellho, et al., Angiology 34: 231–243 (1983); Frederick, et al., Science 224: 289–290 (1980); Burgos, Eur. J. Clin. Invest 13: 289–296 (1983); and Catellot, et al., Proc. Natl Acad. Sci. 79: 5597–5601 (1982), all of which show the existence of angiogenic factors in normal tissues.

Characteristic of all of the angiogenic materials discussed in the above referenced prior art is that they are involved in normal growth and development. In other words, angiogenesis is a necessary process during the growth and development of an individual organism. The prior art angiogenic factors described supra are involved in these normal processes, but are apparently not implicated in enhanced rates of angiogenesis, which is sometimes necessary or desirable.

The first research into factors provoking enhanced angiogenesis is to be found in Goldsmith, et al., JAMA 252: 2034–2036 (1984). The factor was found in chloroform-methanol fractionates of feline omentum. This research is presented in U.S. Pat. No. 4,699,788, the disclosure of which is incorporated herein. This extract is a lipid extract.

Additional research based upon the teachings of Goldsmith, et al. found that the class of glycolipids known as gangliosides possesses enhanced angiogenic activity. This may be seen in U.S. Pat. No. 4,710,490, the disclosure of which is incorporated by reference herein.

It will be seen that the newest research on angiogenesis points to lipid containing molecules as provoking enhanced angiogenesis. This was new to the art, as the earlier literature all suggested that protein derived material caused angiogenesis. Thus, Kumar, et al., Lancet 2: 364–367 (1983) teach proteins of from 300 to 105 daltons, while Kissun, et al., Br. J. Ophthalmol 66: 165–169 (1982), show protein factors weighing up to 70 kilodaltons. Banda, et al., Proc. Natl. Acad. Sci. 79: 7773–7777 (1982), teach proteins of from 2 to 14 kilodaltons as provoking angiogenesis and Burgos, et al., Eur. J. Clin. Invest 13: 289–296 (1983), show protein complexes of from 100 to 200 kilodaltons. A very recent report, by van Brunt, et al., Biotechnology 6(1): 25–30 (Jan. 1988) describes angiogenesis caused by proteins.

The art, however, contains no mention of angiogenesis, either normal or enhanced, caused by oligosaccharides "Oligosaccharides" as defined, e.g., by Steadman's Medical Dictionary (Williams & Wilkins, 1982), Baltimore, at 980, are compounds "made up of the condensation of a small number of monosaccharide units". For purposes of this application, the "small number" referred to by Steadman's is defined to be 2 or greater, as well as monosaccharides which contain at least one substituted group. Monosaccharides, of course, are the building blocks of oligosaccharides, sugars, carbohydrates, and starches, and are components of other materials, such as glycoproteins, glycolipids, and other larger, more complex molecules. Various monosaccharides are well known to the art including, but not being limited to glucose, galactose, mannose, etc. The art also knows that these monosaccharides interact with each other to form various polysaccharide or oligosaccharide materials. When these interact, they form bonds therebetween, which are represented by the carbon number of the participating monosaccharide and the conformation resulting from the bond (alpha or beta). Thus, the nomenclature $1\overset{\alpha}{-}4$ will mean that bonding took place between the first carbon of one monosaccharide and the fourth carbon of another, and the bond is in alpha configuration. The skilled artisan will be familiar with the terminology and nomenclature of oligosaccharide chemistry, and will recognize that the foregoing is merely one example of a myriad of possible oligosaccharide configurations, both simple and complex.

It has now been found that many oligosaccharides cause angiogenesis. The ability to cause this phenomenon does not appear to be linked to any bond configuration, number of monosaccharide units, or constituents of the molecule. In order to determine which oligosaccharides are and are not angiogenic, a simple mechanism is available. Such a method is described herein.

Hence it is an object of the invention to provide a method for causing angiogenesis in a subject in need of angiogenesis, comprising administering to said subject an angiogenically effective amount of an angiogenically active, pharmaceutically acceptable oligosaccharide. This administration may take a number of forms, and the oligosaccharide may be administered alone, or with other pharmaceutically acceptable substances, such as pharmaceutically acceptable carriers.

How this object, and other objects of the invention are accomplished will be seen from the disclosure which follows:

DETAILED DESCRIPTION OF PREFERRED EMBODIMENTS

Table of Oligosaccharides

As alluded to supra oligosaccharide structure is complex, and nomenclature is cumbersome. For this reason, the following table gives structures and full names of all of the oligosaccharides used in the examples which follow. Abbreviations, rather than full names, will be used.

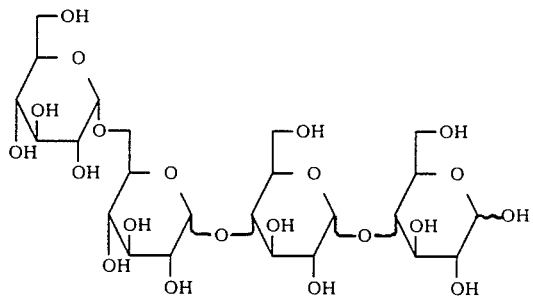

O—α-D-glucopyranosyl-(1→6)-O—α-D-glucopyranosyl-(1→4)-O—α-D-glucopyranosyl-(1→4)-D-glucose
Formula: $C_{24}H_{42}O_{21}$
MW: 666.6

Glc1$\xrightarrow{\alpha}$6Glc1$\xrightarrow{\alpha}$4Glc1$\xrightarrow{\alpha}$4Glc

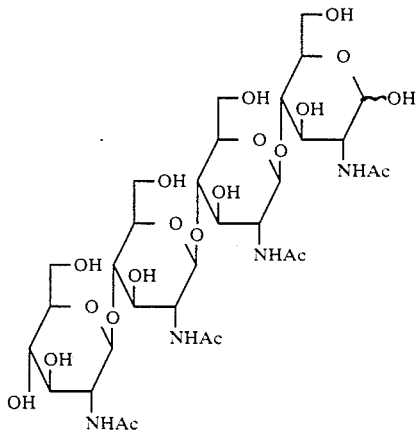

O—(2-Acetamido-2-deoxy-β-D-glucopyranosyl-(1→4)-O—2-(2-acetamido-2-deoxy-β-D-glucopyranosyl-(1→4)-O—(2-acetamido-2-deoxy-β-D-glucopyranosyl)-(1→4)2-acetamido-2-deoxy-D-glucose
(N,N',N'',N'''-Tetraacetyl chitotetraose)
Formula: $C_{32}H_{54}O_{21}N_4$
MW: 830.8

GlcNAc1$\xrightarrow{\beta}$4GlcNAc1$\xrightarrow{\beta}$4GlcNAc1$\xrightarrow{\beta}$4GlcNAc

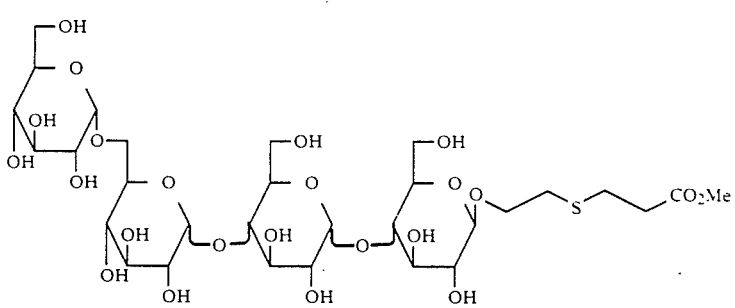

2-(2-Carbomethoxyethylthio)ethyl O—α-D-glucopyranosyl-(1→6)-O—α-D-glucopyranosyl-(1→4)-O—α-D-glucopyranosyl-(1→4)-β-D-glucopyranoside
Formula: $C_{30}H_{52}O_{23}S$
MW: 812.8

Glc1$\xrightarrow{\alpha}$6Glc1$\xrightarrow{\alpha}$4Glc1$\xrightarrow{\alpha}$4Glc-β-O—CETE

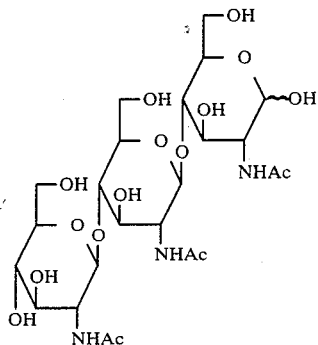

O—(2-acetamido-2-deoxy-β-D-glucopyranosyl-(1→4)-O—(2-acetamido-2-deoxy-β-D-glucopyranosyl)-(1→4)-2-acetamido-2-deoxy-D-glucose
(N,N',N''-Triacetyl chitotriose)
Formula: $C_{24}H_{41}O_{16}N_3$
MW: 627.6

GlcNAc1$\xrightarrow{\beta}$4GlcNAc1$\xrightarrow{\beta}$4GlcNAc

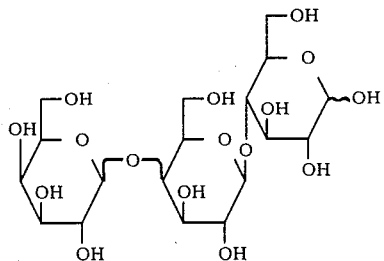

O—β-D-Galactopyranosyl-(1→4)-O—β-D-galactopyranosyl-(1→4)-D-glucose
Formula: $C_{18}H_{30}O_{16}$
MW: 504.5

Gal1$\xrightarrow{\beta}$4Gal1$\xrightarrow{\beta}$4Glc

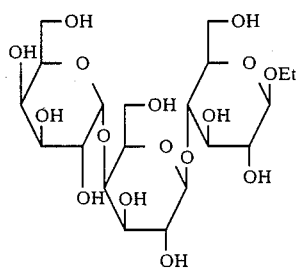

Ethyl O—α-D-galactopyranosyl-(1→4)-O—β-D-galactopyranosyl-(1→4)-β-D-glucopyranoside
Formula: $C_{20}H_{34}O_6$
MW: 532.5

Gal1$\xrightarrow{\alpha}$4Gal1$\xrightarrow{\beta}$4Glc-β-O—Et

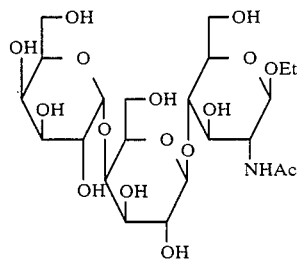

Ethyl O—α-D-galactopyranosyl-(1→4)-O—β-D-galactopyranosyl- (1→4)-2-acetamido-2-deoxy-β-D-glucopyranoside
Formula: $C_{22}H_{37}O_{16}N$
MW: 573.6

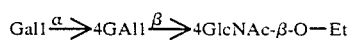

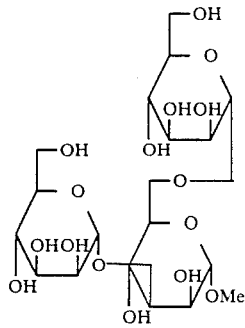

Methyl O—α-D-mannopyranosyl-(1→6)-[O—α-D-mannopyranosyl-(1→3)]-α-D-mannopyranoside
Formula: $C_{19}H_{34}O_{16}$
MW: 518.5

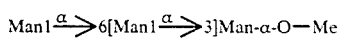

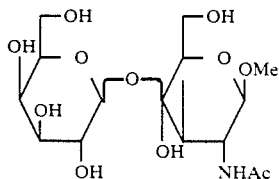

Methyl O—β-D-galactopyranosyl-(1→3)-2-acetamido-2-deoxy-β-D-glucopyranoside
Formula: $C_{15}H_{27}O_{11}N$
MW: 397.4

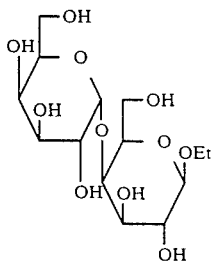

Ethyl O—α-D-galactopyranosyl-(1→4)-O—β-D-galactopyranoside
Formula: $C_{14}H_{26}O_{11}$
MW: 370.4

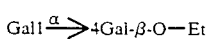

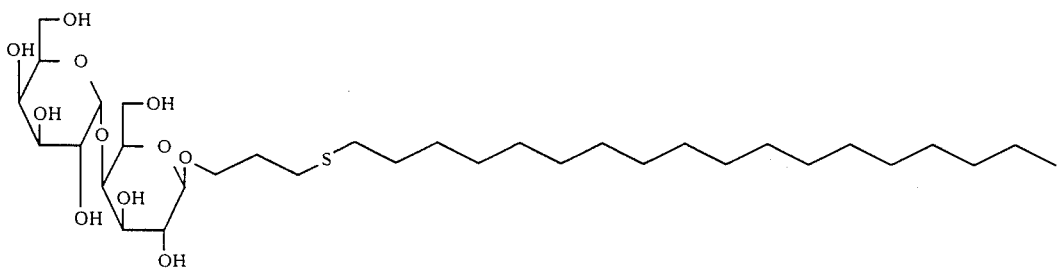

2-(Octadecylthio)ethyl O—α-D-galactopyranosyl-(1→4)-β-D-galactopyranoside
Formula: $C_{32}H_{62}O_{11}S$

MW: 654.9

Gal1$\xrightarrow{\alpha}$4Gal-β-O—OTE

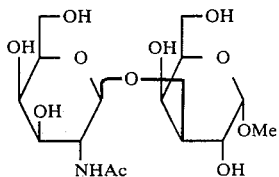

Methyl O—(2-acetamido-2-deoxy-β-D-galactopyranosyl)-(1→3)-α-D-galactopyranoside
Formula: $C_{15}H_{27}O_{11}N$
MW: 397.4

GalNAc1$\xrightarrow{\beta}$3Gal-α-O—Me

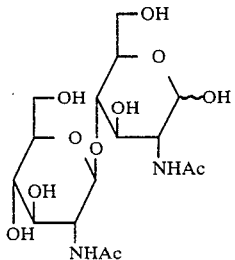

O—(2-Acetamido-2-deoxy-β-D-glucopyranosyl)-(1→4)-2-acetamido-2-deoxy-D-glucose
(N,N'-Diacetyl chitobiose)
Formula: $C_{16}H_{28}O_{11}N_2$
MW: 424.4

GlcNAc1$\xrightarrow{\beta}$4GlcNAc

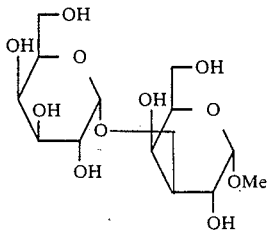

Methyl O—α-D-galactopyranosyl-(1→3)-α-D-galactopyranoside
Formula: $C_{13}H_{24}O_{11}$
MW: 356.4

Gal1$\xrightarrow{\alpha}$3Gal-α-O—Me

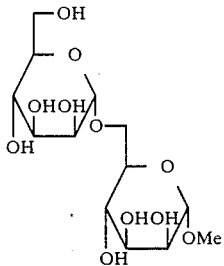

Methyl O—α-D-mannopyranosyl-(1→6)-α-D-mannopyranoside
Formula: $C_{13}H_{24}O_{11}$
MW: 356.4

Man1$\xrightarrow{\alpha}$6Man-α-O—Me

-continued

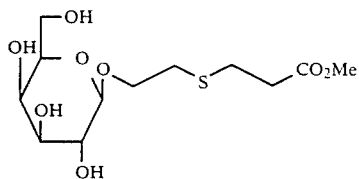

2-(2-Carbomethoxyethylthio)ethyl β-D-galactopyranoside
Formula: $C_{12}H_{22}O_8S$
MW: 326.4
Gal-β-O—CETE

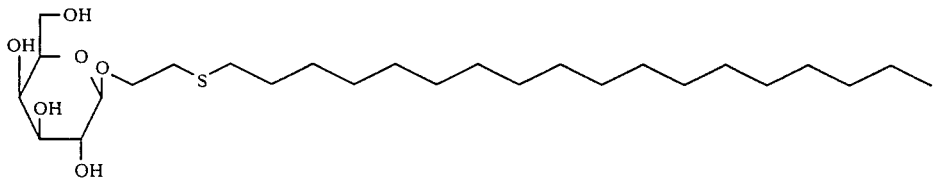

2-(Octadecylthio)ethyl β-D-galactopyranoside
Formula: $C_{26}H_{52}O_6S$
MW: 492.8

Gal-β-O—OTE

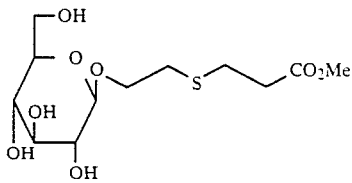

2-(2-Carbomethoxyethylthio)ethyl β-D-glucopyranoside
Formula: $C_{12}H_{22}O_8S$
MW: 326.4
Glc-β-O—CETE

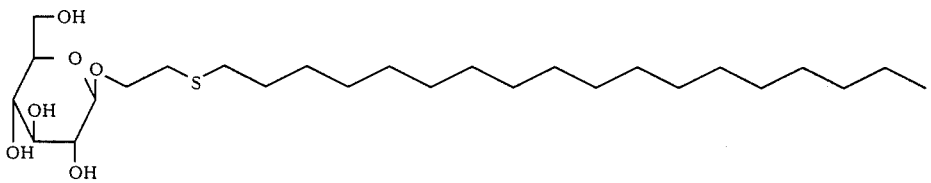

2-(Octadecylthio)ethyl β-D-glucopyranoside
Formula: $C_{26}H_{52}O_6S$
MW: 492.8
Glc-β-O—OTE Following this Table of oligosaccharides is a table giving the abbreviation which will be used for all residues used

| Residues | Abbreviation |
| --- | --- |
| D-Galactose | Gal |
| N—Acetyl-D-galactosamine | GalNAc |
| D-Glucose | Glc |
| N—Acetyl-D-glucosamine | GlcNAc |
| D-Mannose | Man |
| 2-(2-Carbomethoxyethylthio)ethyl | CETE |
| Bovine Serum Albumin | BSA |
| 2-(Octadecylthio)Ethyl | OTE |
| Ethyl | Et |
| Methyl | Me |

The ability of the oligosaccharide compounds to provoke angiogenesis was determined via performing Chick Embryo Chorioallantoic Membrane Assays ("CAM" assays, hereafter), and by calculating "Discriminator Values" or "DU" values. These methods were described in U.S. Pat. No. 4,710,490, which also shows the usefulness of these methods in determining angiogenicity of a substance.

The CAM Assays

These assays involved removing a 2 cm² piece of shell from a fertilized egg on its fourth day of incubation. This "window" was tightly sealed off from the environment with cellophane tape. The windowed eggs were then incubated for another four days, at 37° C.

On the eight day after fertilization, 0.4 g of agarose and 10 ml of phosphate buffered saline (PBS) were mixed and heated to 100° C. in a glass vial. This was mixed, at 50° C., with a 2% solution of bovine serum albumin (BSA) in PBS. The mixture was warmed in a water bath, and 50 μg (calculated amount) of the compound being tested was mixed with a drop of agarose, with constant stirring. A disc formed, via gelation, which was then cut to size.

The cut discs were applied, on the eighth day of incubation, inside the egg on the chorioallantoic membrane. The discs were placed approximately 1 cm away from the chick embryo but not so far away that the disc was beyond the CAM or stuck to the inside shell wall. The eggs were then incubated for another four days.

After twelve days of incubation, the discs were located within the eggs, and the windows were enlarged by breaking off additional bits of shell, using forceps.

The eggs were then examined under a light microscope for vascularization. The degree of vascularization around the disc was compared to the vascularization in the rest of the egg. This "neovascularization" is given a rating, on a scale of 0 to 5, i.e.:

0: no effect—negative;
1: one or two small areas of increased branching around the disc. This is essentially a negative response;
2: three or more small areas of increased branching around the disc; a weak response;
3: formation of "wheel spoke effect", which is self explanatory; increased branching around the disc; a moderate response;
4: "wheel spoke effect" with further increased branching around the disc; a strong response;
5: wheel spoke effect with extensive branching around the disc. This is a very strong response.

Plus and minus values are used also, so that a particular CAM assay could have a score of 0, 0+, 1−, 1, 1+, 2−, 2, 2+, 3−, 3, 3+, 4−, 4, 4+, 5− or 5.

Based on this scoring system, the ANGIOGENIC INDEX ("A Index" or "A" in the following discussion) is determined. The A Index permits comparative analysis of samples, in terms of angiogenic activity, and is defined by:

$$A = \frac{\Sigma \text{ assay scores}}{\text{Maximum Possible Score}} \times 100\%$$

For example, if twelve CAM assays are run on a compound, the maximum score is sixty. If five are zero; four are one; is one is three; and one is four; the A Index is:

$$\frac{5(0) + 4(1) + 1(2) + 1(3) + 1(4)}{60} \times 100\% = 21.67$$

With reference to the compounds in given supra, the A values (and distribution) are given in Table 1. Compounds are indicated by abbreviated name, rather than full name. The distribution is given in terms of negative (0 or 1); weak (2), moderate (3) or strong (4 and 5).

TABLE 1

| Compound | N | W | M | S | A Value |
|---|---|---|---|---|---|
| Man 1 −α→ 6(Man 1 −α→ 3)Man−α−O | 9 | 1 | 0 | 0 | 24.72 |
| Glc−β−O−Cete | 7 | 1 | 0 | 0 | 23.38 |
| Glc−β−O−OTE | 11 | 1 | 0 | 0 | 24.52 |
| Glcα1 −→ 6Glcα1 −→ 4Glcα1 −→ 4Glc | 0 | 12 | 4 | 0 | 45.90 |

TABLE 1-continued

| Compound | N | W | M | S | A Value |
|---|---|---|---|---|---|
| Glc 1 −α→ 6Glc −α→ 4Glc −α→ 4Glc−β-CETE | 2 | 9 | 2 | 0 | 41.09 |
| GlcNAc1 −β→ 4GlcNAc1 −β→ 4GlcNAC | 0 | 12 | 0 | 0 | 44.53 |
| GlcNAC1 −β→ 4GlcNAc1 −β→ 4GlcNAC1 −β→ 4GlcNAc | 0 | 12 | 1 | 0 | 43.12 |
| GlcNAC1 −β→ 4GlcNAC | 4 | 6 | 0 | 0 | 33.36 |
| Gal−β-O−Cete | 0 | 7 | 3 | 0 | 46.76 |
| Gal−β-O−OTE | 5 | 6 | 0 | 0 | 30.36 |
| Galα1 −→ 3Gal−α-O−Me | 7 | 6 | 0 | 0 | 29.80 |
| Galα1 −→ 4Gal−β-O−OTE | 2 | 7 | 1 | 0 | 37.38 |
| Galα1 −→ 4Gal−β-O−Et | 1 | 10 | 2 | 0 | 45.23 |
| Galα1-Galβ1 −→ 4Glc−β-O−Et | 4 | 11 | 1 | 0 | 37.98 |
| Galα1 −→ 4Galβ1 −→ 4GlcNAc−β-O−Et | 3 | 7 | 0 | 0 | 33.36 |
| Gal 1 −β→ 3GlcNAc−β-O−Me | 0 | 3 | 5 | 0 | 49.23 |
| Galβ1 −→ 4Galβ1 −→ 4Glc | 0 | 6 | 2 | 0 | 44.23 |
| GalNAc1 −β→ 3Gal−α-O−Me | 3 | 10 | 1 | 0 | 36.23 |
| Manα1 −→ 6Man−α-O−Me | 6 | 2 | 0 | 0 | 25.90 |
| Control | 7 | 1 | 0 | 0 | 20.07 |
| Control | 7 | 0 | 0 | 0 | 20.06 |
| Control | 12 | 1 | 0 | 0 | 16.46 |

"A Indices" are only one measure of a compound's angiogenicity. While the values given are a good indicia of what compounds are promising, a much more meaningful quantity is the DU value, because these values take into consideration not only the A value, but the percent negative of a given compound.

Mean values $s_I$ and $S_I$, for compounds of a given class I, as well as the values $s_{II}$ and $S_{II}$, for a class II are taken. These numbers represent centroids of distribution for each class of compounds, and are used to determine "weight coefficients", i.e., $W_1$ and $W_2$ and $X_{1T}$ and $X_{2T}$, where $$W_1 = S_{II} - S_I \quad X_{1T} = \frac{S_{II} + S_I}{2}$$

$$W_2 = s_{II} - s_I \quad X_{2T} = \frac{s_{II} + s_I}{2}$$

-continued $$DU = S_I \frac{W_1}{(W_1^2 + W_2^2)^{\frac{1}{2}}} + S_{II} \frac{W_2}{(W_1^2 + W_2^2)^{\frac{1}{2}}}$$

The smaller the DU value, the greater the angiogenic properties of the sample.

Another value "T" is also determined. T is equal to $$X_{1T}\left[\frac{W_1}{(W_1^2 + W_2^2)^{\frac{1}{2}}}\right] + X_{2T}\left[\frac{W_2}{(W_1^2 + W_2^2)^{\frac{1}{2}}}\right]$$

and gives a "cutoff" value for angiogenicity. For a given compound, a DU value, less than T indicates that it is angiogenic, and a higher value, that it is not. For the oligosaccharides, as a whole, that value of T is 26.6.

DU values for the above identified oligosaccharides are as follows:

| Compound | DU value |
|---|---|
| Man1 $\xrightarrow{\alpha}$ 6(Man1 $\xrightarrow{\alpha}$ 3) $\longrightarrow$ Man—α-O | 66.64 |
| Glc—β-O—Cete | 65.11 |
| Glc—β-O—Ote | 68.20 |
| Glcα1 $\longrightarrow$ 6Glcα1 $\longrightarrow$ 4Glcα1 $\longrightarrow$ 4Glc | −22.31 |
| Glc1 $\xrightarrow{\alpha}$ 6Glc $\xrightarrow{\alpha}$ 4Glc $\xrightarrow{\alpha}$ 4Glc $\longrightarrow$ β-Cete | −6.52 |
| GlcNAc1 $\xrightarrow{\beta}$ 4GlcNAc1 $\xrightarrow{\beta}$ 4GlcNAc | −21.64 |
| GlcNAc1 $\xrightarrow{\beta}$ 4GlcNAc1 $\xrightarrow{\beta}$ 4GlcNAc1 $\xrightarrow{\beta}$ 4GlcNAC | −20.96 |
| GlcNAc1 $\xrightarrow{\beta}$ 4GlcNAC | 18.75 |
| Gal—β-O—Cete | −22.72 |
| Gal—β-O—Ote | 24.97 |
| Galα1 $\longrightarrow$ 3Gal—α-O—Me | 32.58 |
| Galα1 $\longrightarrow$ 4Gal—β-OtE | −0.69 |
| Galα1 $\longrightarrow$ 4Gal—β-O—Et | −15.26 |
| Galα1 $\longrightarrow$ 4Galβ1 $\longrightarrow$ 4Glc $\longrightarrow$ β-O—Et | 3.39 |
| Galα1 $\longrightarrow$ 4Galβ1 $\longrightarrow$ 4GlcNAc—β-O—Et | 10.01 |
| Gal1 $\xrightarrow{\beta}$ 3GlcNAc—β-O—Me | −23.92 |
| Galβ1 $\longrightarrow$ 4Galβ1 $\longrightarrow$ 4Glc | −21.49 |
| GalNAc1 $\xrightarrow{\beta}$ 3Gal—α-O—Me | 1.12 |
| Manα1 $\longrightarrow$ 6Man—α-O—Me | 52.96 |

It will be seen from the foregoing data that there is no discernable pattern which emerges as to which classes of oligosaccharides are angiogenic, and which are not.

Additional experiments were then carried out, using oligosaccharides conjugated to bovine serum albumin (BSA). A indices, and DU values were obtained, using the same protocol described supra. For each of the following compounds, it is to be understood that there is a conjugated BSA molecule.

TABLE 3

| BSA Containing Compound | Distribution | | | | A Index |
|---|---|---|---|---|---|
| | N | W | M | S | |
| (GalNAc—β-O—Cete)$_N$ | 0 | 14 | 1 | 0 | 43.17 |
| (GlcNAc—β-O—Cete)$_N$ | 0 | 6 | 10 | 0 | 52.56 |
| (CH$_3$—O—Cete)$_N$ | 3 | 7 | 1 | 0 | 38.27 |
| (Gal1 $\xrightarrow{\beta}$ 3GalNAc—β-O—Cete)$_N$ | 5 | 6 | 1 | 0 | 36.75 |
| (Gal1 $\xrightarrow{\alpha}$ 4Gal—β-O—Cete)$_N$ | 4 | 5 | 1 | 0 | 35.4 |
| (Glc1 $\xrightarrow{\alpha}$ 6Glc1 $\xrightarrow{\alpha}$ 4Glc1—β-O—Cete) | 8 | 4 | 0 | 0 | |
| (Gal1β $\longrightarrow$ 3GlcNAc—β-O—Cete)$_N$ | 3 | 10 | 3 | 0 | 40.46 |

TABLE 3-continued

| BSA Containing Compound | Distribution N | W | M | S | A Index |
|---|---|---|---|---|---|
| Gall —α→4Gall —β→4GlcNAc—β-O—Cete)$_N$ | 5 | 8 | 1 | 0 | 34.8 |
| (LactNAc—β-O—Cete)$_N$ | 0 | 6 | 2 | 0 | 47.58 |

The DU values for these compounds are in Table 4

TABLE 4

| BSA Ctg Compound | Du |
|---|---|
| (GalNAc—β-O—Cete)$_N$ | −20.98 |
| (GlcNAc—β-O—Cete)$_N$ | −25.54 |
| (CH$_3$—O—Cete)$_N$ | 5.24 |
| (Gall —β→3GalNA—β-O—Cete)$_N$ | 18.56 |
| (Gall —α→4Gal—β-O—Cete)$_N$ | 17.75 |
| (Glcl —α→6Glcl —α→4Glcl—β-O—Cete)$_N$ | |
| (Gall —β→3GlcNAc—β-O—Cete)$_N$ | −3.28 |
| (Gal —α→4Gal—β-4GlcNAc—β-O—Cete) | 14.3 |
| (LactNAc—β-O—Cete)$_N$ | −23.12 |

It will be seen from these values that all of the tested BSA containing complexes were angiogenic. A further test was run in which compounds were tested in uncomplexed, and BSA complexed forms:

TABLE 5

| Compound | DU value uncomplexed | DU value complexed |
|---|---|---|
| Lact—β-O—Cete | 77.68 | −21.09 |
| Manl —α→6[Manl —α→3]Man—α-O—Cete | 66.64 | −16.44 |
| Glc—β-O—Cete | 65.11 | 1.76 |
| LactNAc—β-O—Cete | 77.1 | −23.11 |

It will be seen, of course, that conjugation to BSA changed the compounds from highly unangiogenic to highly angiogenic.

Additional angiogenic studies were performed on the oligosaccharide fraction of human milk, Kobata e.g., in Meth. Enzym. 28: 262–271 (1972); Kobata, The Glycoconjugates, Vol. 1, pp. 423–440 (Academic Press, 1978), describe human milk oligosaccharides in general. Many different oligosaccharides are present in milk. They contain up to eleven sugar residues, consisting for the most part of sialic acid, fucose, galactose, N-acetylglucosamine, and glucose. Oligosaccharides in milk are derived from nine core oligosaccharides, i.e., lactose; lacto-N-tetraose; neo-lacto-N-tetraose; lacto-N-hexaose, neo-lacto-N-hexaose; para-lacto-H-hexaose; lacto-N-octaose, and neo-lacto-N-octaose, with peripheral occurrence of sialic acid and fucose. Four types of fucose linkages and three types of sialic acid linkages have been described, giving rise to many possible structures.

For these experiments, the method described by Egge, et al., Arch. Biochem. Biophys. 224: 235 (1983) was followed to obtain total human milk neutral oligosaccharide fractions. While many components were present the major components were lactose; lacto-N-tetraose; lacto-N-neotetraose, and lacto-difuco tetraose. Their structures are as follows (as per Newburg, et al., *Human Lactation* 2 (Hamosh, et al., ed., 1986):

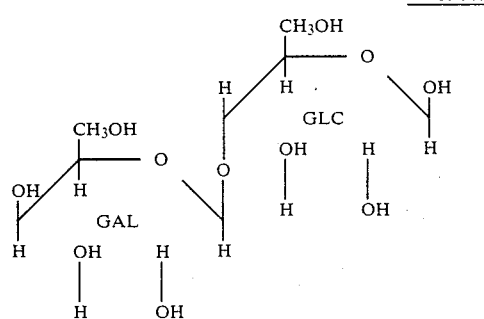

FIG. 3
Structures of Neutral Oligosaccharides

LACTOSE

-continued
FIG. 3
Structures of Neutral Oligosaccharides
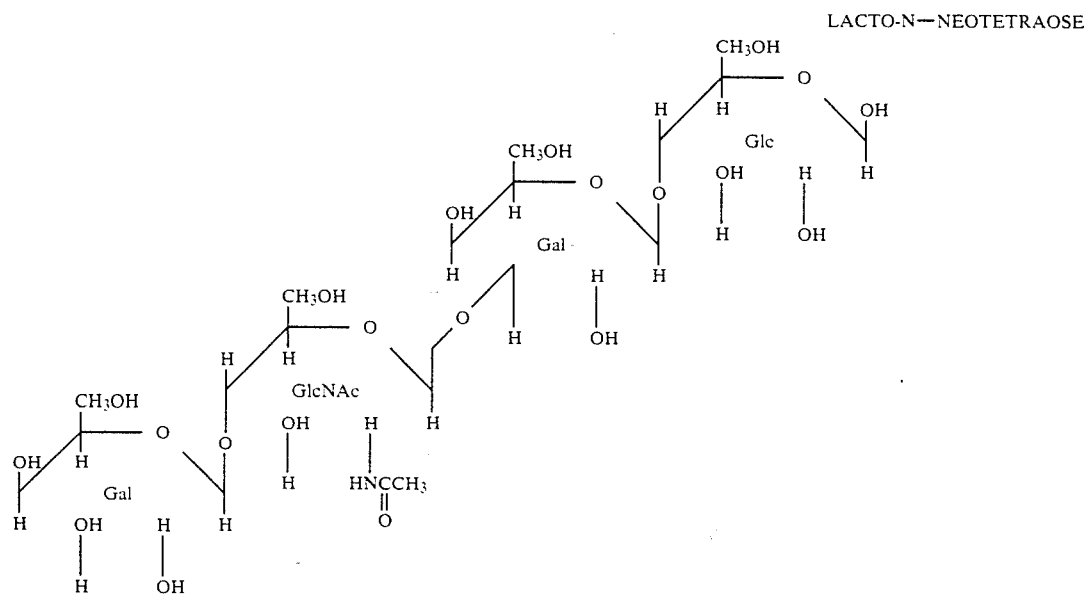
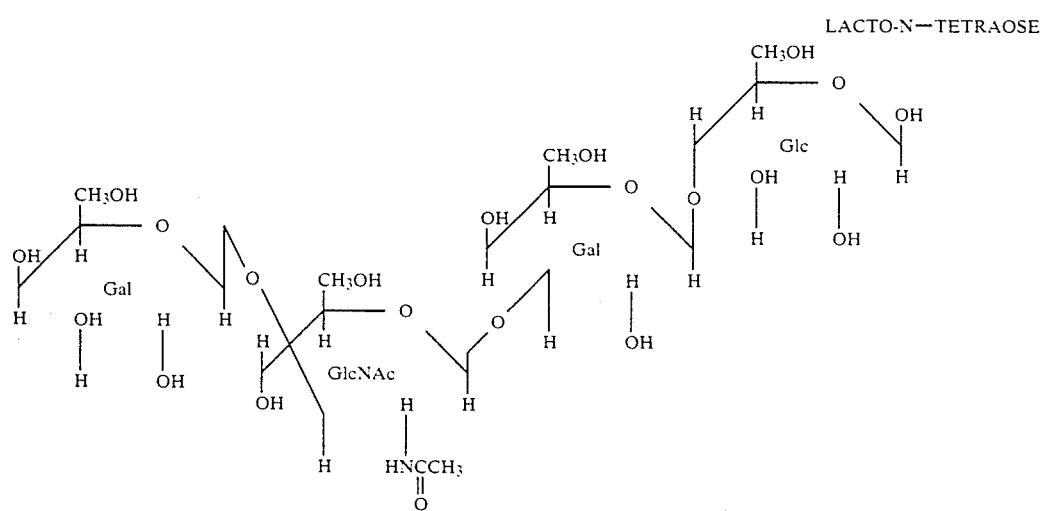

-continued
FIG. 3
Structures of Neutral Oligosaccharides

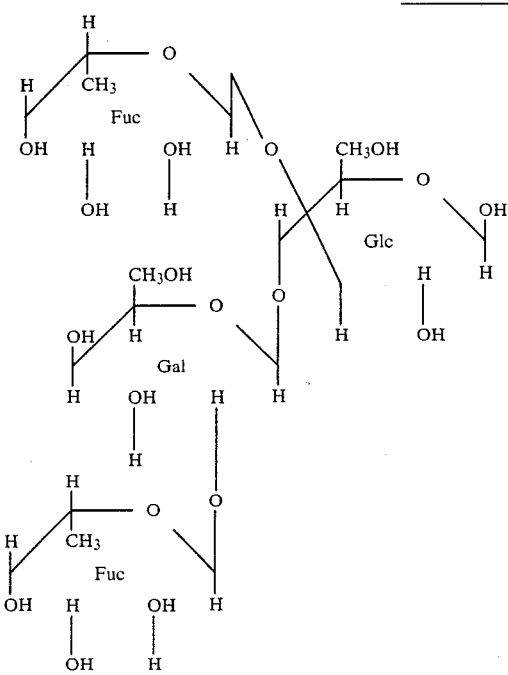

LACTODIFUCOTETRAOSE

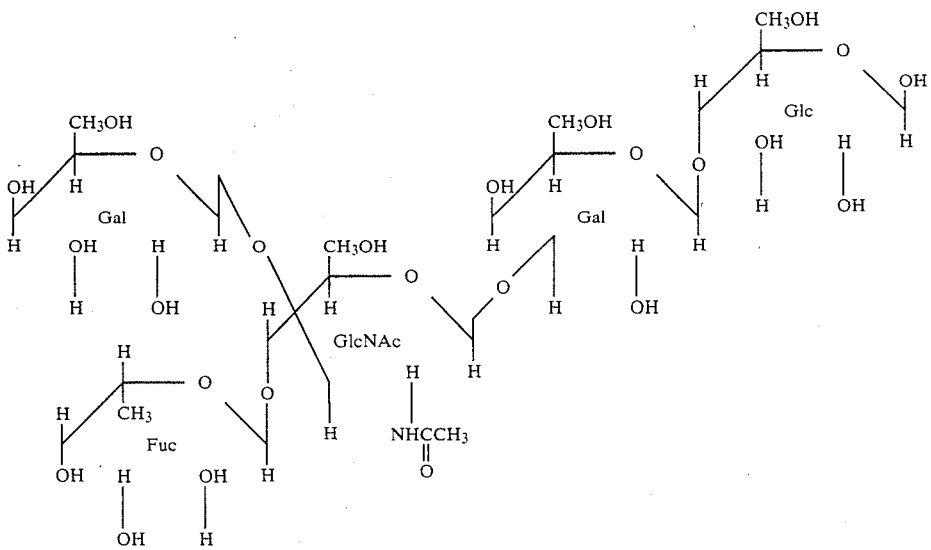

LACTO-N—FUCOPENTAOSE II

Once the human milk oligosaccharides were obtained, their angiogenicity was assayed, using the same CAM assay as described supra, but at varying concentrations. The results were as follows:

| Human Milk Oligosaccharide Calculated Amount | Distribution | | | | A value | DU |
|---|---|---|---|---|---|---|
| | N | W | M | S | | |
| 12.5 μg | 0 | 6 | 4 | 0 | 48.1 | −23.28 |
| 25.0 μg | 0 | 4 | 4 | 0 | 50.93 | −24.75 |
| 50.0 μg | 0 | 2 | 7 | 0 | 54.13 | −26.31 |
| 100.00 μg | 0 | 5 | 5 | 0 | 52.08 | −25.31 |
| 150.00 μg | 0 | 9 | 1 | 0 | 47.46 | −23.07 |
| 200.00 μg | 0 | 10 | 0 | 0 | 44.78 | −21.76 |

Another set of experiments were carried out which tested the angiogenicity of human milk oligosaccharides.

In order to study the angiogenicity of human milk oligosaccharides, a CAM assay which differs from the assay described supra was performed.

In order to test samples, methyl cellulose pellets were used. These pellets were prepared by first autoclaving a sample of methyl cellulose dry, followed by dissolving (2% w/v) in sterile distilled water. This solution was mixed by overnight stirring.

The methyl cellulose solution was used to prepare both the control pellets used in the CAM assays, as well as the sample pellets.

To prepare sample pellets, methylcellulose solution was poured onto 100 mm. Petri dish covers, and this solution was then allowed to dry. The dried methyl cellulose formed a thin layer which was cut into 0.5 cm² squares.

Measured amounts of human milk oligosaccharides (200 µg; 150 µg; 100 µg; 99 µg; 50 µg; 30 µg; 25 µg; 12.5 µg; 10 µg and 3 µg) were added to each square in a PBS solution, and allowed to dry.

The pellets were then used in CAM assays following Auerbach, et al., Developmental Biology 41: 391–4 (1974). Four day old fertilized chicken eggs were cracked into plastic Petri dishes. The Petri dishes containing embryos were then incubated in 37° C. humidity incubator for another five days. On day nine of the incubation the pellets bearing either the test substance or control were applied to the CAM. The eggs were examined 48 and 72 hours after application of the pellets. The CAMs were then scored as positive ("+") or negative ("−") using the criteria based upon the published work of Folkman et al., Int. Rev. Exp. Path., 16: 207 (1976). A positive response is the production of a "spoke-wheel" pattern around the pellet.

The results were as follows:

| Amount | Angiogenic Score (Positive/Total) | % Positive |
|---|---|---|
| 200 µg/egg | 7/11 | 63.6 |
| 150 µg/egg | 6/11 | 54.5 |
| 100 µg/egg | 5/12 | 41.7 |
| 99 µg/egg | 10/23 | 43.5 |
| 50 µg/egg | 0/15 | 0.0 |
| 30 µg/egg | 5/22 | 22.7 |
| 25 µg/egg | 1/10 | 10.0 |
| 12.5 µg/egg | 0/15 | 0.0 |
| 10 µg/egg | 1/10 | 10.0 |
| 3 µg/egg | 3/12 | 25.0 |

The foregoing results show that pharmaceutically acceptable angiogenically active oligosaccharides can be used to provoke or to enhance angiogenesis. Thus, to one skilled in the art, it will be clear that angiogenesis can be accomplished by administering an angiogenically effective amount of oligosaccharide or oligosaccharides to the host in need of angiogenesis. Typically, although not exclusively, this can be accomplished via injection, either as the oligosaccharide itself, or admixed with a pharmaceutically acceptable carrier, such as water or saline solution, as well as other diluents, fillers, etc., known to the skilled artisan and being pharmaceutically acceptable.

The amount of oligosaccharides administered to the patient depends upon various parameters, including the mode administration, the patient's general health, additional pathological conditions, and so forth. What constitutes an effective amount is thus dependent on many factors. Generally, though daily administration of from about 100 µg to about 20 mg per day, regardless of mode of administration, is the preferred dosage for a human being. This dosage frequently, although not necessarily, is administered in several smaller amounts during the course of a given day.

Various classes of oligosaccharides have been shown to be effective as angiogenic agents in the results set forth supra. It will be seen that tetrasaccharides, trisaccharides, and disaccharide molecules can all be angiogenically active. Additionally, the data show angiogenic activity in oligosaccharides which are composed entirely of glucose, entirely of galactose, and of mannose, as well as mixtures thereof.

The given examples, of course, do not cover all oligosaccharides in existence; nonetheless it is submitted that the examples provide such a simple and easy way to determine whether or not an oligosaccharide is angiogenic that, to the skilled artisan, it becomes a matter of simple routine, given this disclosure, to determine other angiogenically active oligosaccharides.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for causing or enhancing angiogenesis in a subject in need thereof, comprising administering to said subject an angiogenically effective amount of at least one angiogenically active oligosaccharide.

2. Method of claim 1, wherein said oligosaccharide is a tetrasaccharide.

3. Method of claim 2, wherein said tetrasaccharide is selected from the group consisting of O-α-D-glucopyranosyl-(1→6)-O-α-D-glucopyranosyl-(1→4-O-α-D-glucopyranosyl-(43 4) 1→4)-D-glucose, · O-(2-Acetamido-2-deoxy-β-D-glucopyranosyl-(1→4)-O-2 (2-acetamido-2-deoxy-β-D-glucopyranosyl)-(1→4)-O-(2-acetamido-2-deoxy-β-D-glucopyranosyl)-(1→4)2-acetamido-2-deoxy-D-glucose (N,N',N",N'''-Tetraacetyl chitotetraose), and 2-(2-Carbomethoxyethylthio)ethyl-O-α-D-glucopyranosyl-(1→6)-O-α-D-glucopyranosyl-(1→4)-O-α-D-glucopyranosyl-(1→4)-β-D-glucopyranoside.

4. Method of claim 1, wherein said oligosaccharide is a trisaccharide.

5. Method of claim 4, wherein said trisaccharide is selected from the group consisting O-(2-acetamido-2-deoxy-β-D-glucopyranosyl-(1→4)-O-(2-acetamido-2-deoxy-β-D-glucopyranosyl)-(1→4)-2-acetamido-2-deoxy-D-glucose (N,N',N"-Triacetyl chitotriose), O-β-D-Galactopyranosyl-(1→4)-O-β-D-galactopyranosyl-(1→4)-D-glucose, Ethyl O-α-D-galactopyranosyl-(1→4)-O-β-D-galactopyranosyl-(1→4)β-D-glucopyranoside, Ethyl O-α-D-galactopyranosyl-(1→4)-O-β-D-galactopyranosyl-(1→4)-2-acetamido-2-deoxy-β-D-glucopyranoside, and Methyl O-α-D-mannopyranosyl-(1→6)-[O-α-D-mannopyranosyl-(1→3)-α-D-mannopyranoside.

6. Method of claim 1, wherein said oligosaccharide is a disaccharide.

7. Method of claim 6, wherein said disaccharide is selected from the group consisting of Methyl O-β-D-galactopyranosyl-(1→3)-2-acetamido-2-deoxy-β-D-glucopyranoside, Ethyl O-α-D-galactopyranosyl-(1→4)-O-β-D-galactopyranoside, 2-(Octadecylthio)ethyl O-α-D-galactopyranosyl-(1→4)-β-D-galactopyranoside, Methyl O-(2-acetamide-2-deoxy-β-D-galactopyranosyl)-(1→3)-α-D-galactopyranoside, O-(2-Acetamido-2-deoxy-β-D-glucopyranosyl)-(1→4)-2-acetamido-2-deoxy-D-glucose (N,N'-Diacetyl chitobiose), Methyl O-α-D-galactopyranosyl-(1→3)-α-D-galactopyranoside, and Methyl O-α-D-mannopyranosyl-(1→6)-α-D-mannopyranoside.

8. Method of claim 1, comprising administering a mixture of oligosaccharides to said subject.

9. Method of claim 8, wherein said mixture of oligosaccharides is derived from human milk.

10. Method of claim 9, wherein said mixture of oligosaccharides contain lactose.

11. Method of claim 9, wherein said mixture of oligosaccharides contains lacto-N-neotetraose.

12. Method of claim 9, wherein said mixture of oligosaccharides contains lactodifucotetraose.

13. Method of claim 9 wherein said mixture of oligosaccharides contains lacto-N-fuco pentaose II.

14. Method of claim 1, wherein said subject is a human being.

15. Method of claim 1, wherein said oligosaccharide is administered in an amount ranging from about 100 μg to about 20 mg per day.

16. Method of claim 1, wherein said oligosaccharide contains only glucose residues.

17. Method of claim 1, wherein said oligosaccharide contains only galactose residues.

18. Method of claim 1, wherein said oligosaccharide contains only mannose residues.

19. Method of claim 1, wherein said oligosaccharide contains a mixture of at least two of glucose, galactose, and mannose residues.

20. Method of claim 1, wherein said oligosaccharide is conjugated to bovine serum albumin.

21. Method of claim 20, wherein said oligosaccharide complexed to obvine serum albumin is selected from the group consisting of O-β-(2-(2-carbomethoxyethylthio)ethyl)-N-acetyl-D-galactosamine; O-β-(2-(2-carboxymethoxyethylthio)ethyl-N-acetyl-D-glucosamine; O-2-(2-carbomethoxyethylthio)ethyl-methyl; and O-β-(2-(2-carboxymethoxyethylthio)ethyl galactose 1-β-3 N-acetyl glucosamine.

22. Method of claim 1, wherein said oligosaccharide is a substituted monosaccharide selected from the group consisting of 2-(2-Carbomethoxyethylthio)ethyl-β-D-galactopyranoside, 2-1-(Octadecylthio)ethyl-β-D-galactopyranoside, 2-(2-Carbomethoxyethylthio)ethyl-β-D-glucopyranoside, and 2-(Octadecylthio)ethyl-β-D-glucopyranoside.

* * * * *